(12) United States Patent
Bach et al.

(10) Patent No.: US 7,482,450 B2
(45) Date of Patent: Jan. 27, 2009

(54) METHOD FOR PRODUCING HIGH-PURITY ORGANOIRIDIUM COMPOUNDS

(75) Inventors: Ingrid Bach, Bad Soden (DE); Philipp Stössel, Frankfurt (DE); Hubert Spreitzer, Viernheim (DE)

(73) Assignee: Merck Patent GmbH (DE)

( * ) Notice: Subject to any disclaimer, the term of this patent is extended or adjusted under 35 U.S.C. 154(b) by 585 days.

(21) Appl. No.: 10/550,976

(22) PCT Filed: Mar. 24, 2004

(86) PCT No.: PCT/EP2004/003087

§ 371 (c)(1),
(2), (4) Date: Sep. 26, 2005

(87) PCT Pub. No.: WO2004/085449

PCT Pub. Date: Oct. 7, 2004

(65) Prior Publication Data

US 2006/0142604 A1    Jun. 29, 2006

(30) Foreign Application Priority Data

Mar. 27, 2003    (DE) ................... 103 14 102

(51) Int. Cl.
*C07F 15/00* (2006.01)
(52) U.S. Cl. .......................................... 546/2; 556/146
(58) Field of Classification Search ................... 546/2; 556/146

See application file for complete search history.

(56) References Cited

U.S. PATENT DOCUMENTS

| 4,539,507 A | 9/1985 | VanSlyke et al. |
| 5,151,629 A | 9/1992 | VanSlyke |
| 2004/0077862 A1 | 4/2004 | Stossel et al. |

FOREIGN PATENT DOCUMENTS

| WO | WO-02/060910 | 8/2002 |

*Primary Examiner*—Porfirio Nazario Gonzalez
(74) *Attorney, Agent, or Firm*—Connolly Bove & Hutz LLP

(57) ABSTRACT

The present invention relates to a process for preparing highly pure tris-ortho-metallated organoiridium compounds and such pure organometallic compounds which may find use as coloring components in the near future as functional components (=functional materials) in a series of different types of applications which can be classed within the electronics industry in the widest sense.

18 Claims, No Drawings

METHOD FOR PRODUCING HIGH-PURITY ORGANOIRIDIUM COMPOUNDS

RELATED APPLICATIONS

This application is a national stage application (under 35 U.S.C. 371) of PCT/EP2004/003087 filed Mar. 24, 2004 which claims benefit to German application 103 14 101.2 filed Mar. 27, 2003.

Organometallic compounds, especially compounds of the $d^8$ metals, will find use as coloring components in the near future as active components (=functional materials) in a series of different types of application which can be classed within the electronics industry in the widest sense.

The organic electroluminescent devices based on organic components (for a general description of the construction, see U.S. Pat. Nos. 4,539,507 and 5,151,629) and their individual components, the organic light-emitting diodes (OLEDs) as well as polymeric light-emitting diodes (PLEDs), have already been introduced onto the market, as shown by the available car radios having organic displays from Pioneer or a razor from Philips with a PLED display. Further products of this type will shortly be introduced. In spite of all of this, distinct improvements are still necessary here for these displays to provide real competition to the currently market-leading liquid crystal displays (LCDs) or to overtake them.

A development in this direction which has emerged in recent years is the use of organometallic complexes which exhibit phosphorescence instead of fluorescence [M. A. Baldo, S. Lamansky, P. E. Burrows, M. E. Thompson, S. R. Forrest, Applied. Physics Letters, 1999, 75, 4-6].

For theoretical reasons relating to spin probability, up to four times the energy efficiency and power efficiency are possible using organometallic compounds. Whether this new development will establish itself depends strongly upon whether corresponding device compositions can be found which can also utilize these advantages (triplet emission=phosphorescence compared to single emission=fluorescence) in OLEDs. The essential conditions for practical use here are in particular a long operative lifetime, a high stability against thermal stress and a low use and operating voltage, in order to enable mobile applications. Secondly, there has to be efficient chemical access to the corresponding highly pure organoiridium compounds. Especially taking into account the scarcity of iridium, this is of crucial importance for the resource-protective exploitation of the compound class specified.

In the literature, several processes have been described for the preparation of tris-ortho-metalated organoiridium compounds. The general access routes, the yields achieved by them and their disadvantages will be laid out briefly hereinbelow using the basic skeleton of the compound class mentioned, fac-tris[2-(2-pyridinyl)-κN)phenyl-κC]iridium(III).

Starting from hydrated iridium(III) chloride and 2-phenylpyridine, fac-tris[2-(2-pyridinyl-κN)phenyl-κC]iridium(III) was obtained in an about 10% yield after a complicated chromatographic purification process [K. A. King, P. J. Spellane, R. J. Watts, J. Am. Chem. Soc., 1985, 107, 1431-1432].

K. Dedeian et al. describe a process starting from iridium (III) tris(acetylacetonate) and 2-phenylpyridine, by which fac-tris[2-(2-pyridinyl-κN)phenyl-κC]iridium(III) was obtained in 45% yield. Analogously to the above-described process, it is necessary in this process too to free the product of impurities by chromatographic processes, and in this case, required by the solubility behavior, halogenated hydrocarbons are used [K. Dedeian, P. I. Djurovich, F. O. Garces, G. Carlson, R. J. Watts, Inorg. Chem., 1991, 30, 1685-1687].

In a third known process, di-μ-chlorotetrakis[2-(2-pyridinyl-κN)phenyl-κC]diiridium(III), which initially has to be prepared in an approx. 72% yield from hydrated iridium(III) chloride and 2-phenylpyridine [S. Spouse, K. A. King, P. J. Spellane, R. J. Watts, J. Am. Chem. Soc., 1984, 106, 6647], is used as a reactant. This is then reacted with 2-phenylpyridine and double molar amounts of silver trifluoromethanesulfonate based on the di-μ-chlorotetrakis[2-(2-pyridinyl)-κN]phenyl-κC]di-iridium(III) compound. After chromatographic purification, the authors obtain tris[2-(2-pyridinyl-κN)phenyl-κC]iridium(III) in 75% yield [M. G. Colombo, T. C. Brunold, T. Riedener, H. U. Gudel, Inorg. Chem., 1994, 33, 545-550]. In addition to the chromatographic purification which is again effected with the aid of halogenated hydrocarbons, the use of double molar amounts of silver trifluoromethanesulfonate based on the di-μ-chlorotetrakis[2-(2-pyridinyl-κN)phenyl-κC]di-iridium(III) is disadvantageous, one reason being that silver traces can barely be removed from the product.

The best process to date was described by P. Stössel et al. in WO 02/060910. This process, consisting of the reaction of iridium(III) tris(acetylacetonate) or of a similar 1,3-diketo chelate complex with a corresponding pyridine-aryl or -heteroaryl compound in the presence of a dipolar protic solvent with vigorous heating for a prolonged period (>20 h), gives very good yields (up to 96%) and likewise very good purities (>99.9%). The description in this disclosure is very good; in repeat experiments, it was also possible to reproduce the appropriate results; however, it was noticeable that the synthesis in some cases did not function as well and under some circumstances no longer functioned at all at irregular intervals or in the case of other ligands. The cause of this was unclear for some time.

In the Table 1 below, these literature data are compared for a better overview, including the comparative experiment carried out in Example 1.

TABLE 1

Literature comparison of known preparation processes

|  | Reference 1 | Reference 2 Literature | Reference 2 Comp. Ex. | Reference 3 | Reference 4 |
|---|---|---|---|---|---|
| Reactants | IrCl$_3$<br>2-phenylpyridine | Ir(acac)$_3$<br>2-phenylpyridine | Ir(acac)$_3$<br>2-phenylpyridine | [Ir(ppy)$_2$Cl]$_2$<br>2-phenylpyridine<br>AgO$_3$SCF$_3$ | Ir(acac)$_3$<br>2-phenylpyridine |
| Solvents | 2-ethoxy-<br>ethanol/<br>water | ethylene<br>glycol | ethylene<br>glycol | none | ethylene<br>glycol |

TABLE 1-continued

Literature comparison of known preparation processes

| | Reference 1 | Reference 2 Literature | Comp. Ex. | Reference 3 | Reference 4 |
|---|---|---|---|---|---|
| Temperature | — | 196°-198° C. | 196°-198° C. | 110° C. | reflux |
| Concentration of iridium reactant | 0.03 mol/l | 0.02 mol/l | 0.02 mol/l | — | 0.1 mol/l |
| Molar ratio of iridium reactants to 2-phenylpyridine | 1:4 | 1:6.3 | 1:6.3 | 1:15 | 1:10 |
| Reaction time | 24 h | 10 h | 10 h | 24 h | 60 h |
| Yield | approx. 10% as a by-product of [Ir(μ-Cl)(ppy)]$_2$ | 45% | 39.3-44.0% | 75% | 92-96% |
| Purity by HPLC | no data | no data | 94.0-96.0% | no data | >99.9% |

Reference 1: K. A. King, P. J. Spellane, R. J. Watts, J. Am. Chem. Soc., 1985, 107, 1431-1432. S. Spouse, K. A. King, P. J. Spellane, R. J. Watts, J. Am. Chem. Soc., 1984, 106, 6647-6653.
Reference 2: K. Dedeian, P. I. Djurovich, F. O. Garces, G. Carlson, R. J. Watts Inorg. Chem., 1991, 30, 1685-1687.
Reference 3: M. G. Colombo, T. C. Brunold, T. Riedener, H. U. Güdel Inorg. Chem., 1994, 33, 545-550.
Reference 4: P. Stössel et al., WO 02/060910.

From this overview, it can be seen easily that the process according to reference 4 is distinctly superior to the other known processes. However, the above-outlined problem of poor yield and of the occasional occurrence of irreproducibility and problems when other ligands are used arise.

It has now been found that, surprisingly, a process, as described below, starting from IR complexes or mixtures of such complexes or mixtures comprising such IR complexes which do have acetylacetonate or diketonate ligands but do not have the high symmetry of iridium(III) tris(acetylacetonate), has distinctly better yields and shorter reaction times than the process according to reference 4. Moreover, this in particular allowed the "inexplicable" reproducibility problems outlined to be eliminated and impressively increase the yields for further ligand systems.

The present invention provides a process for preparing homoleptic Ir(III) complexes of the formula (I)

formula (I)

in which:
CyD is a cyclic group which contains at least one donor atom, preferably nitrogen or phosphorus, via which the cyclic group is bonded to the metal and which may in turn bear one or more substituents R; the CyD and CyC groups are joined together via a covalent bond;
CyC is a cyclic group which contains a carbon atom via which the cyclic group is bonded to the metal and which may in turn bear one or more substituents R;
R is the same or different at each instance and is H, F, Cl, Br, I, NO$_2$, CN, a straight-chain, branched or cyclic alkyl or alkoxy group having from 1 to 20 carbon atoms, in which one or more nonadjacent CH$_2$ groups may be replaced by —O—, —S—, —NR$^1$—, —CONR$^2$—, —CO—O—, —CR$^1$=CR$^1$— or —C≡C—, and in which one or more hydrogen atoms may be replaced by F, or an aryl, aryloxy, arylamine or heteroaryl group which has from 4 to 14 carbon atoms and may be substituted by one or more non-aromatic R radicals; where a plurality of substituents R, both on the same ring and on the two different rings, together may in turn form a further mono- or polycyclic, aliphatic or aromatic ring system;
R$^1$ and R$^2$ are the same or different at each instance and are H or an aliphatic or aromatic-hydrocarbon radical having from 1 to 20 carbon atoms, characterized by the reaction of an iridium(III)-containing reactant which contains at least one diketonate structural unit of the formula (II)

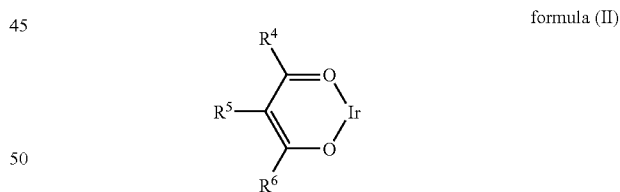

formula (II)

in which:
R$^4$, R$^6$ are the same or different at each instance and are a linear, branched or cyclic alkyl group having 1-20 carbon atoms, in which one or more nonadjacent CH$_2$ groups may be replaced by —O—, —S—, —NR$^1$—, —CONR$^2$—, —CO—O—, —CR$^1$=CR$^1$— or —C≡C—, and in which one or more hydrogen atoms may be replaced by F or aromatic groups each having from 3 to 14 carbon atoms, or an aryl and/or heteroaryl group having 3-20 carbon atoms or an alkoxy group OR$^1$,
R$^5$ is the same or different at each instance and is a linear, cyclic or branched alkyl group having 1-20 carbon atoms, in which one or more nonadjacent CH$_2$ groups may be replaced by —O—, —S—, —NR$^1$—, —CONR$^2$—, —CO—O—, —CR$^1$=CR$^1$— or —C≡C—, and in which one or more hydrogen atoms may be replaced by F or aromatic groups each having from 3 to 14 carbon atoms, or an aryl and/or heteroaryl group having 3-20 carbon atoms, R$^1$ and R$^2$ are the same or different at each instance and are H or an aliphatic or aromatic hydrocarbon radical having from 1 to 20 carbon atoms, excluding homoleptic diketonate complexes of the formula (II) and compounds of the formula (II) which contain two ligands of the formula (III)

formula (III)

where the CyC and CyD radicals in formula (III) are each as defined under formula (I), with a compound of the formula (IV)

formula (IV)

in which the CyD and CyC radicals are each as defined under formula (I).

The diketone formed in the reaction is removed by means of known methods and the target compound is isolated.

A homoleptic complex is understood to mean a complex in which only the same type of ligands are bonded to a metal. The opposite would be a heteroleptic complex in which different ligands are bonded to a metal.

The process according to the invention is illustrated by scheme 1.

Scheme 1:

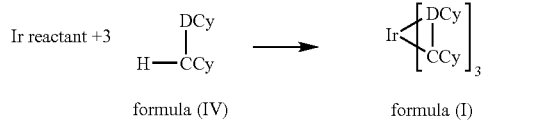

Preferred inventive iridium(III)-containing reactants of the formula (II) are characterized in that they contain a structure of the formula (V)

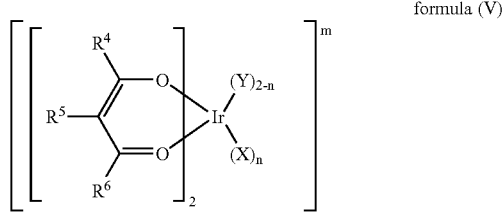

formula (V)

where R$^4$, R$^5$ and R$^6$ are each as defined under formula (II) and the iridium metal is hexacoordinated by the four oxygen atoms of the diketonate ligands and two monodentate ligands which may either be anionic (X) or uncharged (Y); n may be 0, 1 or 2. The complex is negatively charged (m=1−) when n equals 2, the complex is uncharged (m=0) when n=1, and positively charged (m=1+) when n=0. The monodentate X and Y ligands may be cis or trans relative to one another.

Preferred inventive iridium(III)-containing reactants contain a compound of the formula (V) in which X is the same or different at each instance and is a fluoride, chloride, bromide or iodide anion.

Particularly preferred iridium(III)-containing reactants contain a compound of the formula (XI)

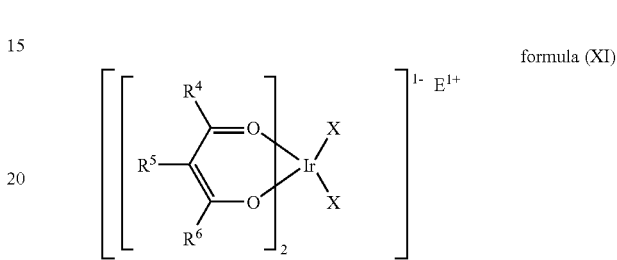

formula (XI)

where R$^4$, R$^5$ and R$^6$ are each as defined under formula (II), X is the same or different at each instance and is a Cl, Br or I anion, and E is an alkali metal cation, ammonium or phosphonium ion. The monodentate X ligands may be cis or trans relative to one another.

Preference is likewise given to iridium(III)-containing reactants which contain a structure of the formula (VI)

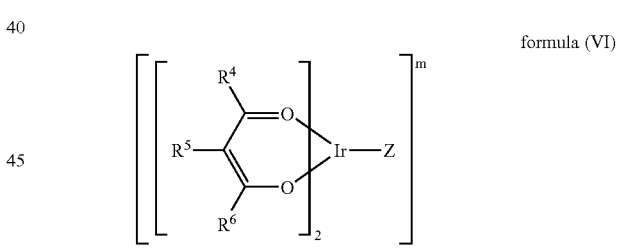

formula (VI)

where R$^4$, R$^5$, R$^6$ are each as defined under formula (II) and where Z, as a bidentate and/or bridging ligand, is bonded to the iridium in a chelating manner and is either an uncharged ligand Z$^0$, for example bipyridine, phenanthroline, ethylenediamine, propylenediamine, or 2-, 3- or 4-aminopyridine, or a monoanionic bidentate ligand Z$^1$, for example diketonate, carboxylate, picolinate, aminocarboxylate or 1-ketoalkoxide, or a dianionic bidentate ligand Z$^2$/for example oxalate, malonate, phthalate, isophthalate, terephthalate, oxide or peroxide. m is 1+ when Z=Z$^0$, 0 when Z=Z$^1$, and 1− when Z=Z$^2$.

Preference is further given to inventive iridium(III)-containing reactants which contain structures of the formula (VII)

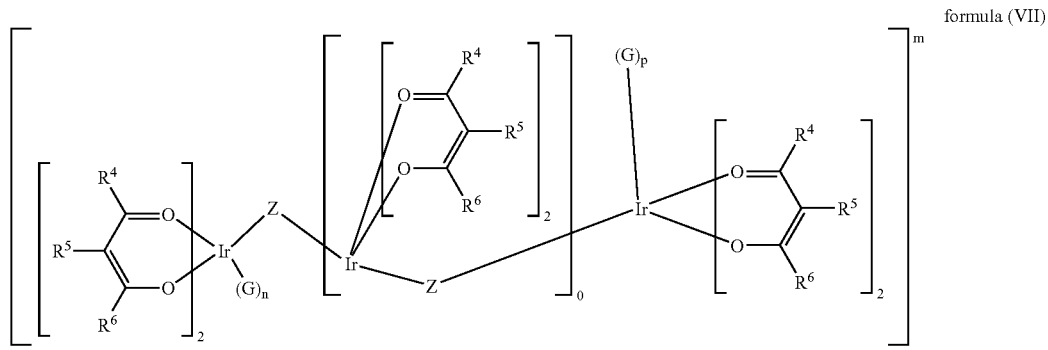

formula (VII)

where $R^4$, $R^5$ and $R^6$ are each as defined under formula (II) and the ligand Z, instead of being bonded in a chelating manner as in formula (VI), is bonded in a bridging manner, so that a plurality of iridium metal atoms which are coordinated simultaneously by two diketonate ligands are bonded to form oligomer-like (o≧2) and polymer-like structures (o to 100 000). G is the same or different at each instance and is either a monovalent anion X or an uncharged monodentate ligand Y. n and p are the same or different at each instance and are 0 or 1. Depending on the selection between uncharged, monoanionic and dianionic, bidentate and/or bridging ligands Z, and also between uncharged and monoanionic, monodentate ligands as end groups G, the resulting structures are multiply positively or negatively charged or uncharged.

Preference is likewise given to inventive iridium(III)-containing reactants which contain structures of the formula (VIII)

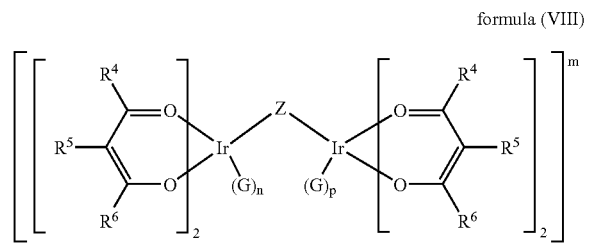

formula (VIII)

in which $R^4$, $R^5$ and $R^6$ are each as defined under formula (II) and the ligand Z which is bidentate and/or bonded in a bridging manner and may be uncharged ($Z^0$), monoanionic ($Z^1$) or dianionic ($Z^2$) joins two iridium metal atoms which are already coordinated by two diketonate ligands bonded in a chelating manner and may each also be bonded to a monodentate uncharged or anionic ligand (G). n and p are the same or different at each instance and are 0 or 1.

Suitable selection of the ligands Z and G gives rise to structures of the formula (VIII) which may be singly or doubly negatively charged (m=1– or 2–), or else singly or doubly positively charged (m=1+ or 2+), or uncharged (m=0). The bridging ligand Z and the monodentate ligand G may be bonded cis or trans relative to one another on the iridium metal.

Preference is further given to inventive iridium(III)-containing reactants which contain structures of the formula (IX)

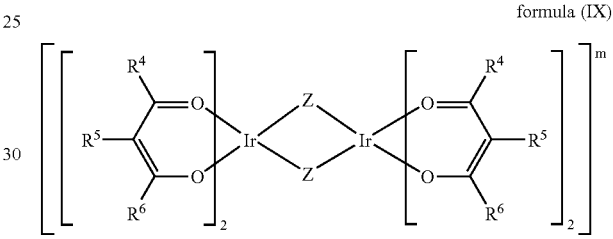

formula (IX)

where $R^4$, $R^5$ and $R^6$ are each as defined under formula (II) and the ligands Z may be bonded in a bridging manner over two iridium metal atoms. Depending on the selection of Z, the iridium-containing reactants may be doubly negatively charged (m=2–) up to doubly positively charged (m=2+). Single charges or uncharged iridium-containing reactants are likewise possible. The iridium is additionally coordinated by four oxygen atoms of the diketonate ligands.

Particular preference is given to iridium(III)-containing reactants which contain structures of the formula (VI), (VII), (VIII) or (IX), characterized in that the uncharged bidentate and/or bridging ligands $Z^0$ are the same or different at each instance and are bipyridine, phenanthroline, ethylenediamine, propylenediamine, or 2-, 3- or 4-aminopyridine.

Particular preference is likewise given to iridium(III)-containing reactants which contain structures of the formula (VI), (VII), (VIII) or (IX) characterized in that the monoanionic bidentate and/or bridging ligands $Z^1$ are the same or different at each instance and are acetylacetonate, carboxylate, for example formate, acetate or propionate, picolinate, aminocarboxylate, for example 2-aminoacetate or 3-aminopropionate, 1-ketoalkoxides, for example tropolonate, benzoin, azide, cyanate, isocyanate, thiocyanate, isothiocyanate, halides, for example chloride, bromide and iodide.

Particular preference is likewise given to iridium(III)-containing reactants which contain structures of the formula (VI), (VII), (VIII) or (IX) in which the dianionic bidentate and/or bridging ligands $Z^2$ are oxalate, malonate, phthalate, isophthalate, terephthalate, oxide or peroxide.

In addition, preference is likewise given to iridium(III)-containing reactants which contain structures of the formula (X)

formula (X)

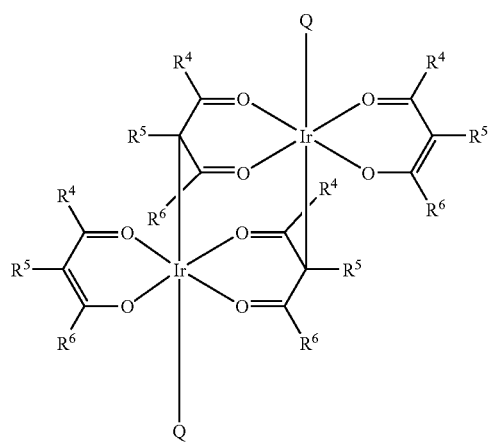

where $R^4$, $R^5$ and $R^6$ are each as defined under formula (II) and Q is a monoanionic monodentate ligand X or a β-diketonate which is bonded to the metal via the carbon atom between the two keto carbon atoms.

Particular preference is given to iridium (III)-containing reactants which contain structures of the formula (X) where Q is a fluoride, chloride, bromide or iodide ion.

Particular preference is given to iridium (III)-containing reactants which contain structures of the formula (V), (VII), (VIII) and/or (IX) and in which X is the same or different at each instance and is a monovalent anion such as $OH^-$, $F^-$, $Cl^-$, $Br^-$, $I^-$, $SCN^-$, $CN^-$, $SH^-$, $SeH^-$, $N_3^-$ alkoxide, nitrate, carboxylate of the formula $R^1COO^-$, cyclopentadienide ($C_5H_5^-$) or hydride ($H^-$).

Particular preference is likewise given to iridium(III)-containing reactants which contain structures of the formula (V), (VII) and/or (VIII) and in which Y is the same or different at each instance and is an uncharged monodentate ligand such as $H_2O$, $H_2S$, a dialkyl sulfide of the formula $(R^1)_2S$, a dialkyl sulfoxide $(R^1)_2SO$, $NH_3$, a primary, secondary or tertiary amine, an alcohol of the formula $R^1OH$, an ether of the formula $(R^1)_2O$, a thiol of the formula $R^1SH$, pyridine, quinoline, a nitrile of the formula $R^1CN$, CO, a phosphine of the formula $P(R^1)_3$, a phosphine oxide of the formula $OP(R^1)_3$, an arsine of the formula $As(R^1)_3$ or a phosphite of the formula $P(OR^1)_3$.

Inventive iridium(III)-containing reactants are likewise mixtures of at least 2 iridium(III)-containing reactants which contain structures of the formula (II), or (V) to (XI).

The synthesis method illustrated here allows iridium(III) complexes of the formula (I) including the iridium(III)-containing reactants (1) to (12) depicted by way of example below to be prepared.

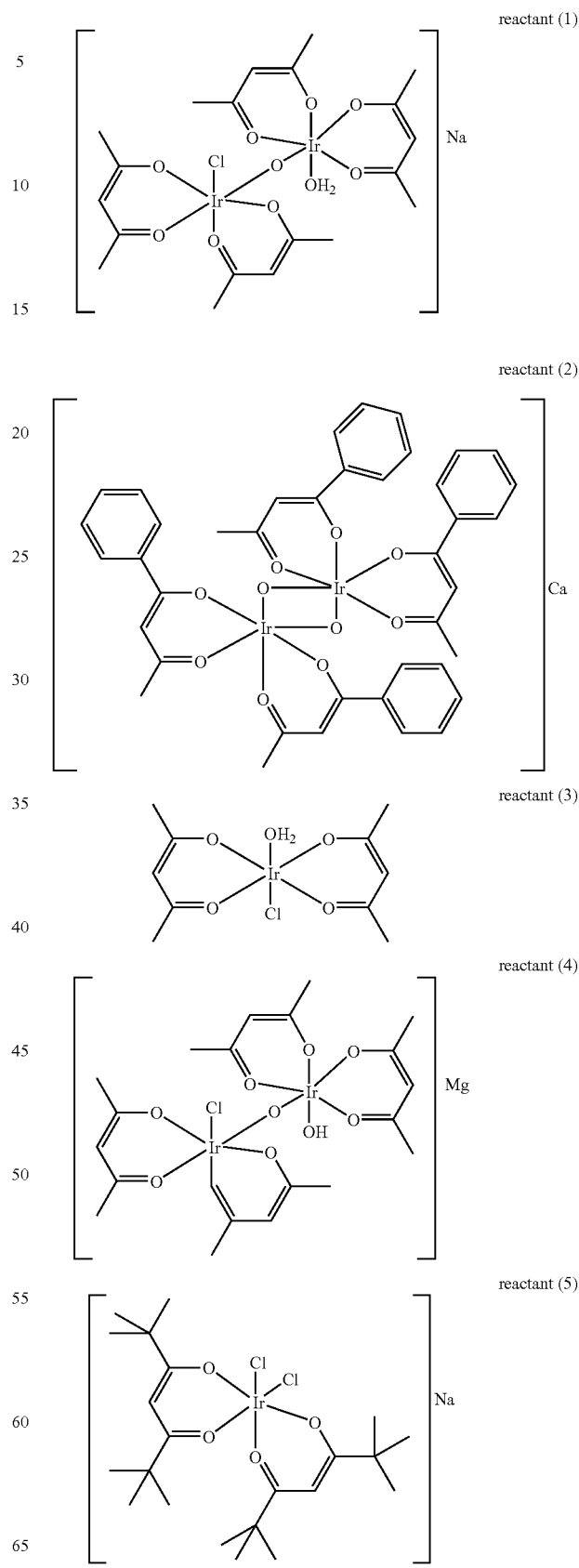

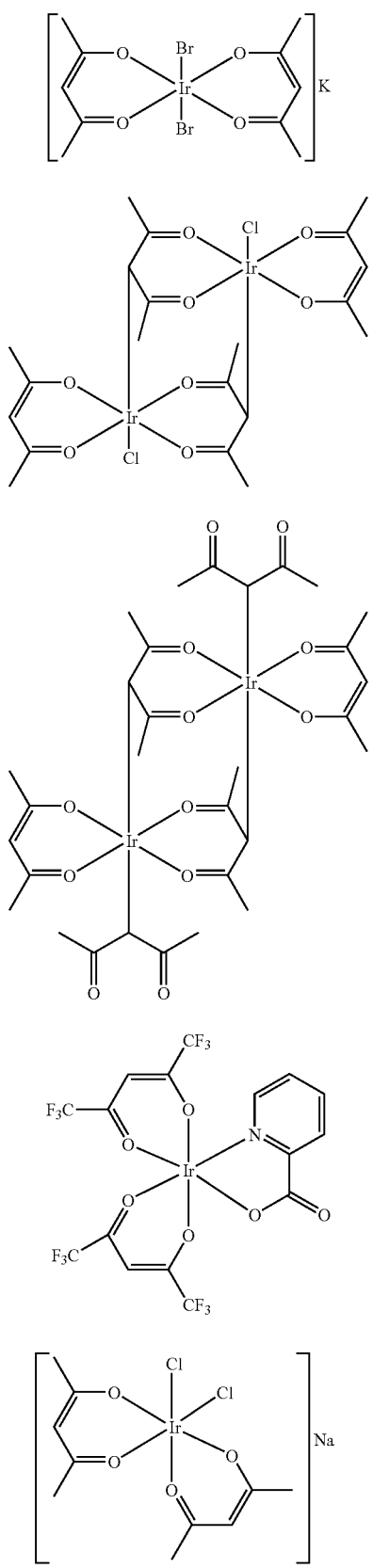

reactant (6)
reactant (7)
reactant (8)
reactant (9)
reactant (10)

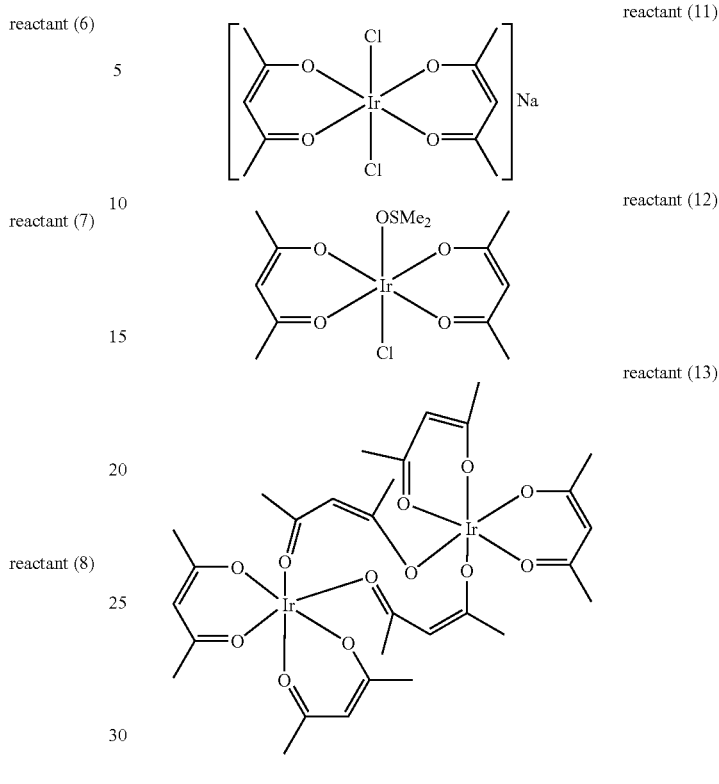

reactant (11)
reactant (12)
reactant (13)

Inventive reaction media are high-boiling dipolar-protic solvents such as ethylene glycol or propylene glycol, or else higher diols or polyalcohols, for example glycerol, or else polyether alcohols such as polyethylene glycols, for example PEG600 and PEG1000, and also their etherified analogs, for example triethylene glycol dimethyl ether or poly(ethylene glycol) dimethyl ether, and also NMP.

According to the invention, the reaction is carried out within a temperature range of from 100° C. to 250° C. According to the invention, the concentration of the iridium (III)-containing reactant is in the range from 0.05 to 1.00 molar.

The inventive molar ratio of the iridium(III)-containing reactant to the ligand of the formula (IV) is from 1:4 to 1:20; preference is given to a ratio of from 1:6 to 1:15; particular preference is given to a ratio of from 1:8 to 1:12.

The preferred concentration of the reactant of the formula (IV) is in the range from 0.50 to 10.00 molar, more preferably in the range from 0.80 to 2.50 molar.

According to the invention, the reaction is carried out within from 20 to 120 h, preferably in the range from 30 to 60 h. A reaction time less than that specified can have the consequence of incomplete conversion of the iridium(III)-containing reactant used, which can lead to yield losses and to contamination of the product with iridium(III)-containing reactant or intermediates.

As can be taken from the examples, some of the compounds of the formula (I) are obtainable via a process according to the prior art only in very moderate yields and purities. The process according to the invention in some cases actually opens up the route to iridium(III) complexes of the formula (I).

This invention therefore further provides homoleptic Ir(III) complexes of the formula (I)

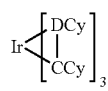

formula (I)

in which CyD, CyC, R, $R^1$ and $R^2$ are each as defined under formula (I), characterized in that they have been obtained by the above-described process.

The compounds obtained by this process have over the compounds according to the prior art that they have greater purity, preferably greater than 99%, more preferably greater than 99.5% (by NMR or HPLC), and are thus better suited to electronic appliances.

The present invention is illustrated in detail by the examples which follow without any intention to restrict it to the examples. It is thus possible for those skilled in the art in the field of organic synthesis, without any further inventive activity, to carry out the inventive reactions on further systems as described above.

EXAMPLES

Synthesis of tris-ortho-metallated organoiridium Compounds

The syntheses which follow were carried out up to the workup under a dry pure nitrogen atmosphere or pure argon atmosphere using carefully dried solvents. The reactants used were purchased from Aldrich (ethylene glycol), ABCR (Na[Ir(acac)$_2$Cl$_2$]) and Heräus (iridium(III) acetylacetonate).

The ligands 1-phenylisoquinoline, 2-phenylpyridine, 2-benzothiophen-2-ylpyridine were prepared by literature methods by Suzuki coupling from the corresponding boronic acids and 2-bromopyridine or 1-chloroisoquinoline.

The syntheses are compiled in Table 2, Examples 1, 3 and 5 being comparative examples according to the prior art, and Examples 2, 4 and 6 being inventive examples.

TABLE 2

| Example | Ligand*** | Ir content (% by wt.) | Iridium(III)- containing reactant | Yield | Purity |
|---|---|---|---|---|---|
| 1* | ppy | 39.29 | Ir(acac)$_3$ | 65.2-67.5% | >98% |
| 2* | ppy | 39.69 | Na[Ir(acac)$_2$Cl$_2$] | 90.1-93.6% | >99.9% |
| 3** | piq | 39.29 | Ir(acac)$_3$ | 40.3-42.8% | >99.0% |
| 4** | piq | 39.69 | Na[Ir(acac)$_2$Cl$_2$] | 87.9-91.7% | >99.8% |
| 5** | btp | 39.29 | Ir(acac)$_3$ | 52.3-55.4% | >37.4% |
| 6** | btp | 39.69 | Na[Ir(acac)$_2$Cl$_2$] | 86.9-89.7% | >99.1% |

*40 h at 200° C., shorter reaction time than described in WO 02/060910
**40 h at 180° C.
***ppy (2-phenylpyridine), btp (2-benzothiophen-2-ylpyridine), piq (1-phenylisoquinoline)

Example 1 (Comparative Example)

fac-tris[2-(2-pyridinyl-κN)phenyl-κC]iridium(III)

(according to: P. Stössel et al., WO 02/060910)

4.90 g (10.0 mmol) of iridium(III) acetylacetonate and 15.52 g (14.3 ml, 100 mmol) of 2-phenylpyridine were added to 100 ml of degassed ethylene glycol. The suspension was heated under reflux (oil bath temperature 200-210° C.) with good stirring for 40 h. After cooling to room temperature, a mixture of 240 ml of ethanol and 60 ml of aqueous 1N hydrochloric acid was poured with stirring into the reaction mixture which contained the fac-tris[2-(2-pyridinyl-κN)phenyl-κC]iridium(III) product in the form of a yellow, finely crystalline precipitate. After stirring for 5 minutes, the precipitate was filtered off with suction through a glass suction filter (P3); the yellow, finely crystalline precipitate was washed three times with 30 ml of a mixture of ethanol and aqueous 1N hydrochloric acid (4:1, v:v), five times with 30 ml of a mixture of ethanol and water (1:1, v:v) and five times with 30 ml of ethanol, and subsequently dried under high vacuum at 80° C. for 5 h and at 200° C. for 2 h. The yield, at a purity of >98% by NMR, was 4.27-4.42 g, corresponding to 65.2-67.5%.

$^1$H NMR (CDCl$_3$): [ppm]=7.84 (m, 3H), 7.58 (m, 6H), 7.48 (m, 3H), 6.82 (m, 6H), 6.69 (m, 6H).

Example 2 (Inventive)

fac-tris[2-(2-pyridinyl-κN)phenyl-κC]iridium(III)

Procedure analogous to Example 1, except that iridium(III) acetylacetonate was replaced by 4.84 g of Na[Ir(acac)$_2$Cl$_2$] (Ir content 39.69%) (10.0 mmol).

The yield, at a purity of >99.9% by HPLC, was 5.90-6.13 g, corresponding to 90.1-93.6%.

$^1$H NMR (CDCl$_3$): [ppm]=see Example 1.

Example 3 (Comparative Example)

fac-tris[2-(2-isoquinolinyl-κN)phenyl-κC]iridium (III)

4.90 g (10.0 mmol) of iridium(III) acetylacetonate and 20.53 g (100 mmol) of 1-phenylisoquinoline were added to 100 ml of degassed ethylene glycol. The suspension was heated under reflux (oil bath temperature 180° C.) with good stirring for 40 h. After cooling to room temperature, a mixture of 240 ml of ethanol and 60 ml of aqueous 1N hydrochloric acid was poured with stirring into the reaction mixture which contained the fac-tris [2-(2-isoquinolinyl-κN)phenyl-κC]iridium(III) product in the form of a red, finely crystalline precipitate. After stirring for 5 minutes, the crystals were filtered off through a glass suction filter (P3); the red, finely crystalline precipitate was washed three times with 30 ml of a mixture of ethanol and aqueous 1N hydrochloric acid (4:1, v:v), five times with 30 ml of a mixture of ethanol and water (1:1, v:v) and five times with 30 ml of ethanol, and subsequently dried under high vacuum at 80° C. for 5 h and at 200° C. for 2 h.

The yield, at a purity of >99.0% by HPLC, was 3.24-3.45 g, corresponding to 40.3-42.8%.

$^1$H NMR (CDCl$_3$): [ppm]=8.96 (m, 3H), 8.19 (m, 3H), 7.73 (m, 3H), 7.63 (m, 6H), 7.15 (d, 3H), 7.10 (d, 3H), 6.97 (m, 6H), 6.86 (m, 3H).

Example 4 (Inventive)

fac-tris[2-(1-isoquinolinyl-κN)phenyl-κC]iridium (III)

Procedure analogous to Example 3, except that iridium(III) acetylacetonate was replaced by 4.84 g of Na[Ir(acac)$_2$Cl$_2$] (Ir content 39.69%) (10.0 mmol).

The yield, at a purity of >99.8% by HPLC, was 7.08-7.38 g, corresponding to 87.9-91.7%.

$^1$H NMR (DMSO): [ppm]=see Example 3.

Example 5 (Comparative Example)

fac-tris[2-(2-pyridinyl-κN)benzo[b]thien-3-yl-κC] iridium(III)

4.90 g (10.0 mmol) of iridium(III) acetylacetonate and 21.13 g (100 mmol) of 2-benzothien-2-ylpyridine were added to 100 ml of degassed ethylene glycol. The suspension was heated under reflux (oil bath temperature 180° C.) with good stirring for 40 h. After cooling to room temperature, a mixture of 240 ml of ethanol and 60 ml of aqueous 1N hydrochloric acid was poured with stirring into the reaction mixture which contained the fac-tris[2-(2-pyridinyl-κN)benzo[b]thien-3-yl-κC]iridium(III) product in the form of a red-brown, finely crystalline precipitate. After stirring for 5 minutes, the crystals were filtered off through a glass suction filter (P3); the red-brown, finely crystalline precipitate was washed three times with 30 ml of a mixture of ethanol and aqueous 1N hydrochloric acid (4:1, v:v), five times with 30 ml of a mixture of ethanol and water (1:1, v:v) and five times with 30 ml of ethanol, and subsequently dried under high vacuum at 80° C. for 5 h and at 200° C. for 2 h.

The yield, at a purity of >37.4% by HPLC, was 4.30-4.56 g, corresponding to 52.2-55.4%.

$^1$H NMR (CD$_2$Cl$_2$): [ppm]=7.73 (m, 3H), 7.53 (m, 6H) 7.35 (m, 3H), 7.05 (m, 3H), 6.76 (m, 3H), 6.63 (m, 3H), 6.56 (m, 3H).

Example 6 (Inventive)

fac-tris[2-(2-pyridinyl-κN)benzo[b]thien-3-yl-κC] iridium(III)

Procedure analogous to Example 3, except that iridium(III) acetylacetonate was replaced by 4.84 g of Na[Ir(acac)$_2$Cl$_2$] (Ir content 39.69%) (10.0 mmol).

The yield, at a purity of >99.1% by HPLC, was 7.15-7.38 g, corresponding to 86.9-89.7%.

$^1$H NMR (CD$_2$Cl$_2$): [ppm]=see Example 5.

What is claimed is:

1. A process for preparing homoleptic Ir(III) complexes of the formula (I)

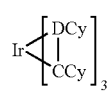

formula (I)

in which:
CyD is a cyclic group which contains at least one donor atom via which the cyclic group is bonded to the metal and which may in turn bear one or more substituents R; the CyD and CyC groups are joined together via a covalent bond;
CyC is a cyclic group which contains a carbon atom via which the cyclic group is bonded to the metal and which may in turn bear one or more substituents R;
R is the same or different at each instance and is H, F, Cl, Br, I, NO$_2$, CN, a straight-chain or branched or cyclic alkyl or alkoxy group having from 1 to 20 carbon atoms, in which one or more nonadjacent CH$_2$ groups may be replaced by —O—, —S—, —NR$^1$—, —CONR$^2$—, —CO—O—, —CR$^1$=CR$^1$— or —C≡C—, and in which one or more hydrogen atoms may be replaced by F, or an aryl or heteroaryl group which has from 4 to 14 carbon atoms and may be substituted by one or more nonaromatic R radicals; where a plurality of substituents R, both on the same ring and on the two different rings, together may in turn form a further mono- or polycyclic, aliphatic or aromatic ring system;

R$^1$ and R$^2$ are the same or different at each instance and are H or an aliphatic or aromatic hydrocarbon radical having from 1 to 20 carbon atoms, characterized by the reaction of an iridium(III)-containing reactant which contains at least one diketonate structural unit of the formula (II)

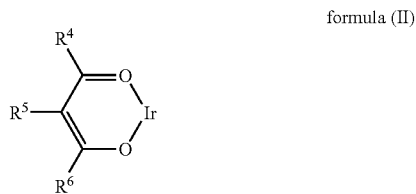

formula (II)

in which:
R$^4$, R$^6$ are the same or different at each instance and are a linear, branched or cyclic alkyl group having 1-20 carbon atoms, in which one or more nonadjacent CH$_2$ groups may be replaced by —O—, —S—, —NR$^1$—, —CONR$^2$—, —CO—O—, —CR$^1$=CR$^1$— or —C≡C—, and in which one or more hydrogen atoms may be replaced by F or aromatic groups each having from 3 to 14 carbon atoms, or an aryl and/or heteroaryl group having 3-20 carbon atoms or an alkoxy group OR$^1$, R$^5$ is the same or different at each instance and is a linear, branched or cyclic alkyl group having 1-20 carbon atoms, in which one or more nonadjacent CH$_2$ groups may be replaced by —O—, —S—, —NR$^1$—, —CONR$^2$—, —CO—O—, —CR$^1$=CR$^1$— or —C≡C—, and in which one or more hydrogen atoms may be replaced by F or aromatic groups each having from 3 to 14 carbon atoms, or an aryl and/or heteroaryl group having 3-20 carbon atoms, R$^1$ and R$^2$ are the same or different at each instance and are H or an aliphatic or aromatic hydrocarbon radical having from 1 to 20 carbon atoms, excluding homoleptic diketonate complexes of the formula (II) and compounds of the formula (II) which contain two ligands of the formula (III)

formula (III)

where the symbols CyC and CyD in formula (III) are each as defined under formula (I), with a compound of the formula (IV)

formula (IV)

in which the symbols CyD and CyC are each as defined under formula (I).

2. The process as claimed in claim 1, characterized in that the iridium(III)-containing reactant contains a structure of the formula (V)

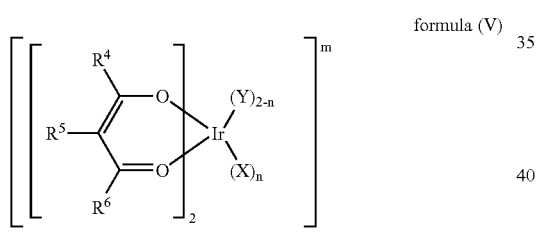

formula (V)

where the symbols $R^4$, $R^5$ and $R^6$ are each as defined in claim 1,
X is the same or different at each instance and is a monovalent anion,
Y is the same or different at each instance and is an uncharged monodentate ligand,
n is 0, 1 or 2 and
m is 1− when n=2, is 0 when n=1 or is 1+ when n=0.

3. The process as claimed in claim 1, characterized in that the iridium(III)-containing reactant contains a structure of the formula (VI)

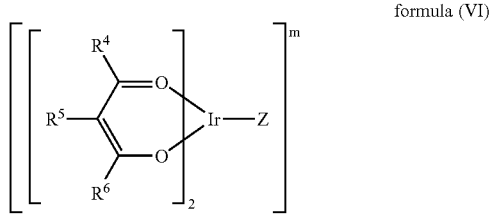

formula (VI)

where $R^4$, $R^5$ and $R^6$ are each as defined in claim 1 and where
Z is the same or different at each instance and is
    and uncharged bidentate and/or bridging ligand $Z^0$,
    a monoanionic bidentate and/or bridging ligand $Z^1$
    or a dianionic bidentate and/or bridging ligand $Z^2$, and
m is 1+ when Z=$Z^0$, is 0 when Z=$Z^1$ and is 1− when Z=$Z^2$.

4. The process as claimed in claim 1, characterized in that the iridium(III)-containing reactant contains a structure of the formula (VII)

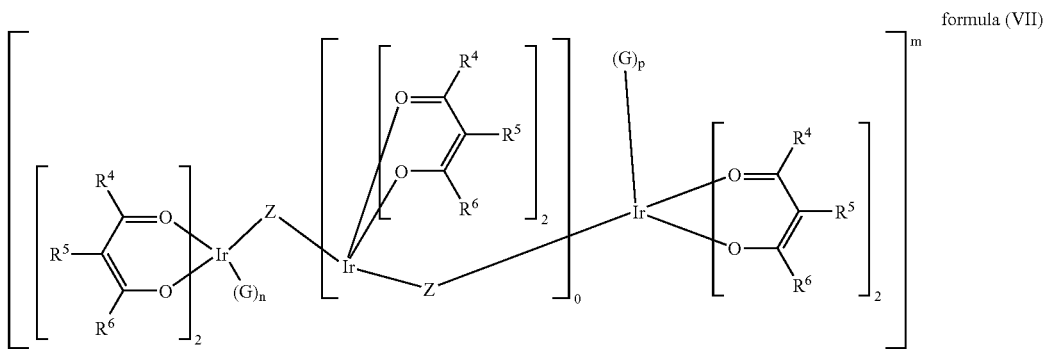

formula (VII)

where $R^4$, $R^5$ and $R^6$ are each as defined in claim 1,
G is the same or different at each instance and is either a monovalent anion X or an uncharged monodentate ligand Y,
Z is the same or different at each instance and is
    and uncharged bidentate and/or bridging ligand $Z^0$,
    a monoanionic bidentate and/or bridging ligand $Z^1$
    or a dianionic bidentate and/or bridging ligand $Z^2$,
n and p are the same or different at each instance and are 0 or 1,
o can assume integer values from 0 to 100 000 and
m may be from (o+2)+ to (o+2)−.

5. The process as claimed in claim 1, characterized in that the iridium(III)-containing reactant contains a structure of the formula (VIII)

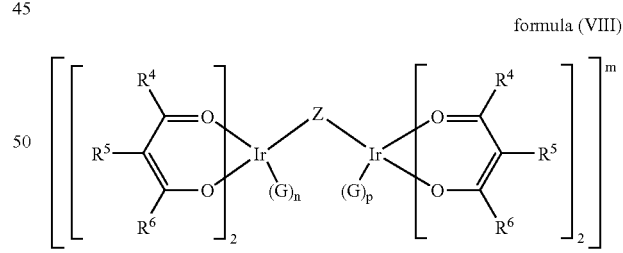

formula (VIII)

where the symbols and indices $R^4$, $R^5$ and $R^6$ are each as defined in claim 1, and in which
G is the same or different at each instance and is either a monovalent anion X or an uncharged monodentate ligand Y
Z is the same or different at each instance and is
    and uncharged bidentate and/or bridging ligand $Z^0$,
    a monoanionic bidentate and/or bridging ligand $Z^1$
    or a dianionic bidentate and/or bridging ligand $Z^2$,
n and p are the same or different at each instance and are 0 or 1, and
m is 2+, 1+, 0, 1− or 2−.

6. The process as claimed in claim 1, characterized in that the iridium(III)-containing reactant contains a structure of the formula (IX)

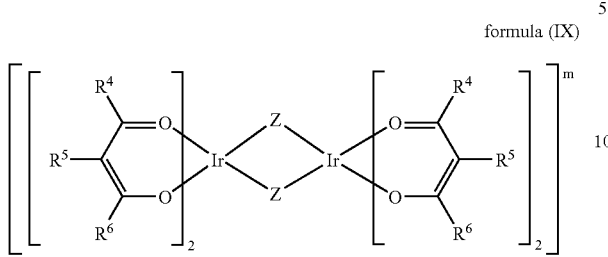

formula (IX)

where the symbols $R^1$, $R^2$, $R^4$, $R^5$ and $R^6$ are each as defined in claim 1 and in which
Z is the same or different at each instance and is
and uncharged bidentate and/or bridging ligand $Z^0$,
a monoanionic bidentate and/or bridging ligand $Z^1$
or a dianionic bidentate and/or bridging ligand $Z^2$ and
m is 2+, 1+, 0, 1– or 2–.

7. The process as claimed in claim 1, characterized in that the iridium(III)-containing reactant contains a structure of the formula (X)

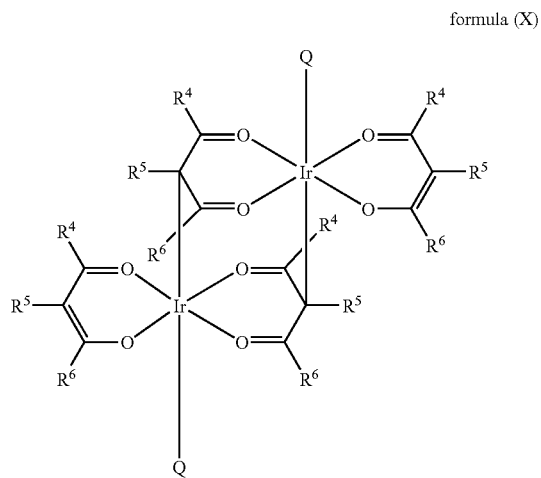

formula (X)

where the symbols $R^4$, $R^5$ and $R^6$ are each as defined in claim 1 and where
Q is the same or different at each instance and is a monovalent anion.

8. The process as claimed in claim 1, characterized in that the iridium(III)-containing reactant contains a compound of the formula (V), (VII) and/or (VIII)

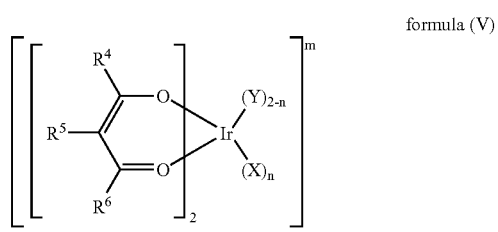

formula (V)

wherein
$R^4$ and $R^6$ are the same or different at each instance and are a linear, branched or cyclic alkyl group having 1-20 carbon atoms, in which one or more nonadjacent $CH_2$ groups may be replaced by —O—, —S—, —$NR^1$—, —$CONR^2$—, —CO—O—, —$CR^1$=$CR^1$— or —C≡C—, and in which one or more hydrogen atoms may be replaced by F or aromatic groups each having from 3 to 14 carbon atoms, or an aryl and/or heteroaryl group having 3-20 carbon atoms or an alkoxy group $OR^1$, $R^5$ is the same or different at each instance and is a linear, branched or cyclic alkyl group having 1-20 carbon atoms, in which one or more nonadjacent $CH_2$ groups may be replaced by —O—, —S—, —$NR^1$—, —$CONR^2$—, —CO—O—, —CR=$CR^1$— or —C≡C—, and in which one or more hydrogen atoms may be replaced by F or aromatic groups each having from 3 to 14 carbon atoms, or an aryl and/or heteroaryl group having 3-20 carbon atoms, Y is the same or different at each instance and is an uncharged monodentate ligand,
n is 0, 1 or 2 and
m is 1– when n=2, is 0 when n=1 or is 1+ when n=0,

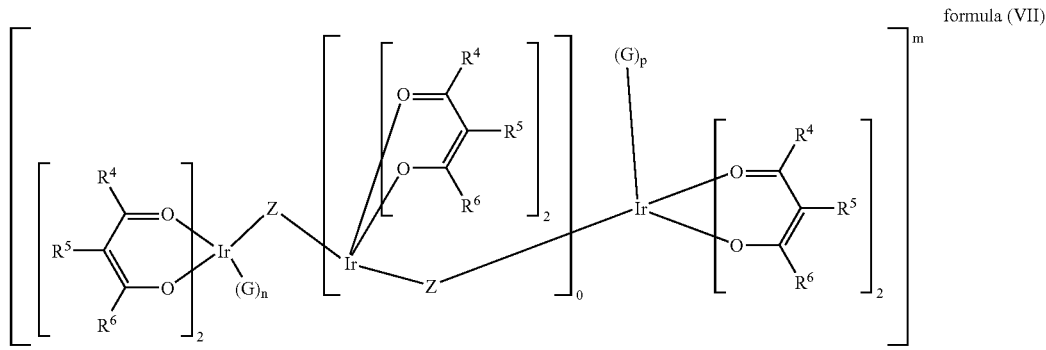

formula (VII)

where $R^4$, $R^5$ and $R^6$ are each as defined above,
G is the same or different at each instance and is either a monovalent anion X or an uncharged monodentate ligand Y,
Z is the same or different at each instance and is and uncharged bidentate and/or bridging ligand $Z^0$, a monoanionic bidentate and/or bridging ligand $Z^1$ or a dianionic bidentate and/or bridging ligand $Z^2$,
n and p are the same or different at each instance and are 0 or 1,
o can assume integer values from 0 to 100 000 and
m may be from (o+2)+ to (o+2)−,

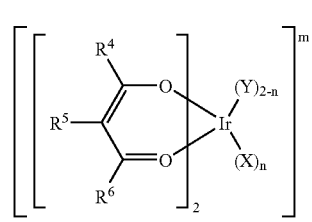

formula (V)

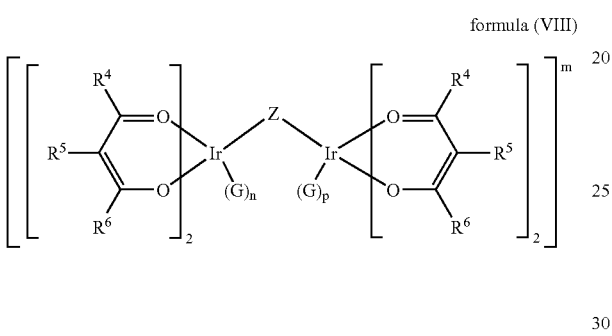

formula (VIII)

where the symbols and indices $R^4$, $R^5$ $R^6$, G, Z, n and p are each as defined above and in which
m is 2+, 1+, 0, 1− or 2−
and X is the same or different at each instance and is $OH^-$, $F^-$, $Cl^-$, $Br^-$, $I^-$, $SCN^-$, $CN^-$, $SH^-$, $SeH^-$, an alkoxide of the formula $R^1O^-$, nitrate, a carboxylate of the formula $R^1COO^-$, cyclopentadienide $(C_5H_5^-)$ or hydride $(H^-)$.

9. The process as claimed in claim 1, characterized in that the iridium(III)-containing reactant contains a compound of the formula (V), (VII) and/or (VIII)

wherein
$R^4$ and $R^6$ are the same or different at each instance and are a linear, branched or cyclic alkyl group having 1-20 carbon atoms, in which one or more nonadjacent $CH_2$ groups may be replaced by —O—, —S—, —$NR^1$—, —$CONR^2$—, —CO—O—, —$CR^1$=$CR^1$— or —C≡C—, and in which one or more hydrogen atoms may be replaced by F or aromatic groups each having from 3 to 14 carbon atoms, or an aryl and/or heteroaryl group having 3-20 carbon atoms or an alkoxy group $OR^1$,
$R^5$ is the same or different at each instance and is a linear, branched or cyclic alkyl group having 1-20 carbon atoms, in which one or more nonadjacent $CH_2$ groups may be replaced by —O—, —S—, —$NR^1$—, —$CONR^2$—, —CO—O—, —$CR^1$=$CR^1$— or —C≡C—, and in which one or more hydrogen atoms may be replaced by F or aromatic groups each having from 3 to 14 carbon atoms, or an aryl and/or heteroaryl group having 3-20 carbon atoms,
n is 0, 1 or 2 and
m is 1− when n=2, is 0 when n=1 or is 1+ when n=0

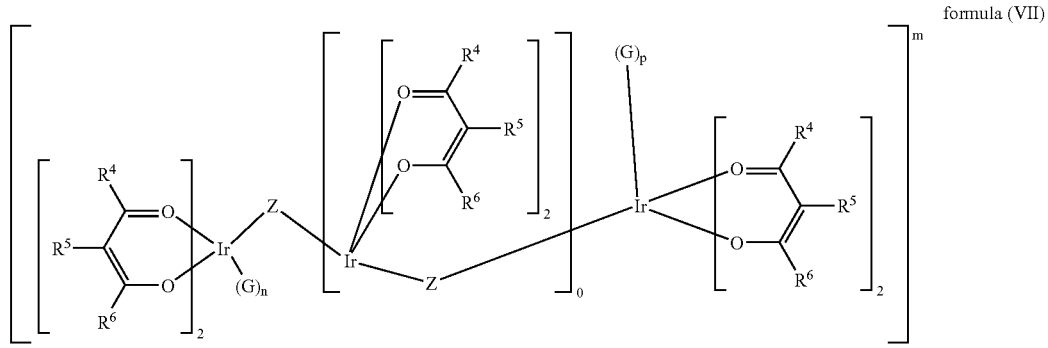

formula (VII)

where $R^4$, $R^5$ and $R^6$ are each as defined above,

G is the same or different at each instance and is either a monovalent anion X or an uncharged monodentate ligand Y, Z is the same or different at each instance and is and uncharged bidentate and/or bridging ligand $Z^0$, a monoanionic bidentate and/or bridging ligand $Z^1$ or a dianionic bidentate and/or bridging ligand $Z^2$, n and p are the same or different at each instance and are 0 or 1, o can assume integer values from 0 to 100 000 and m may be from (o+2)+ to (o+2)−, formula $R^1SH$, an alcohol of the formula $R^1OH$, an ether of the formula $(R^1)_2O$, a dialkyl sulfoxide $(R^1)_2SO$, $NH_3$, a primary, secondary or tertiary amine, pyridine, quinoline, a nitrile of the formula $R^1CN$, CO, a phosphine of the formula $P(R^1)_3$, a phosphine oxide of the formula $OP(R^1)_3$, an arsine of the formula $As(R^1)_3$ or a phosphite of the formula $P(OR^1)_3$.

10. The process as claimed in claim 1, characterized in that the iridium(III)-containing reactant is a compound of the formula (VI), (VII), (VIII) and/or (IX)

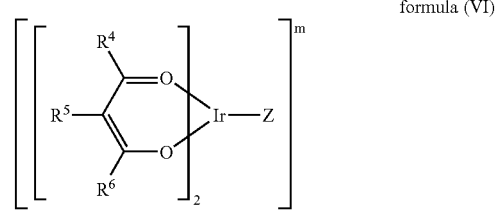

formula (VI)

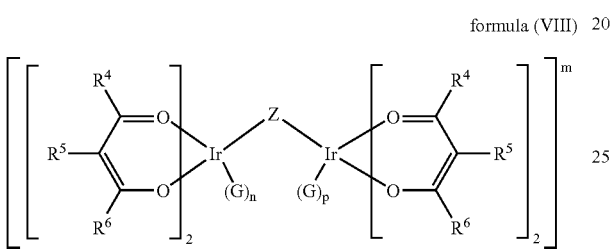

formula (VIII)

where the symbols and indices $R^4$, $R^5$ $R^6$, G, Z, n and p are each as defined above and in which m is 2+, 1+, 0, 1− or 2−, and Y is the same or different at each instance and is $H_2O$, $H_2S$, a dialkyl sulfide of the formula $(R^1)_2S$, a thiol of the where $R^4$, $R^5$ and $R^6$ are each as defined in claim 1 and where Z is the same or different at each instance and is and uncharged bidentate and/or bridging ligand $Z^0$, a monoanionic bidentate and/or bridging ligand $Z^1$ or a dianionic bidentate and/or bridging ligand $Z^2$, and m is 1+ when $Z=Z^0$, is 0 when $Z=Z^1$ and is 1− when $Z=Z^2$,

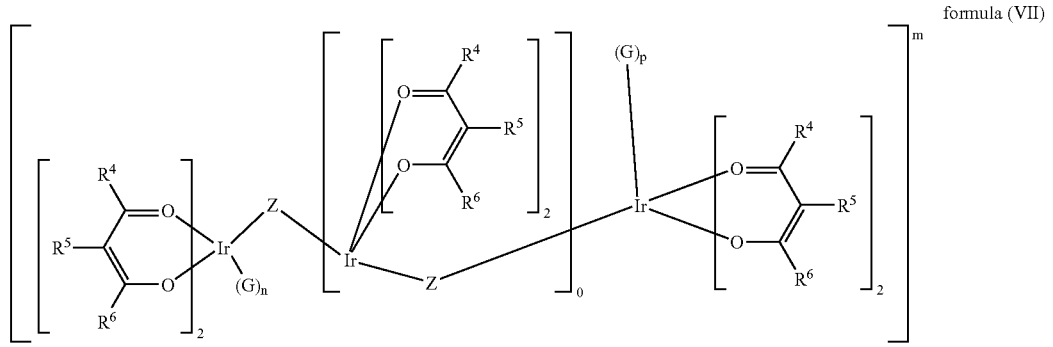

formula (VII)

where $R^4$, $R^5$ and $R^6$ are each as defined in claim 1,
G is the same or different at each instance and is either a monovalent anion X or an uncharged monodentate ligand Y,
n and p are the same or different at each instance and are 0 or 1,
o can assume integer values from 0 to 100 000 and
m may be from (o+2)+ to (o+2)−

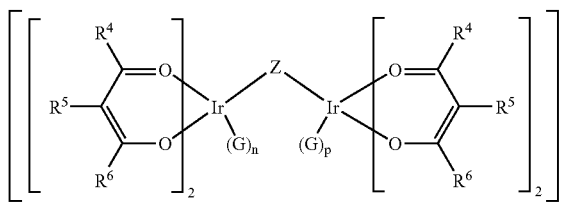

formula (VIII)

where the symbols and indices $R^4$, $R^5$ and $R^6$, G, Z, n and p are each as defined above, m is 2+, 1+, 0, 1− or 2−

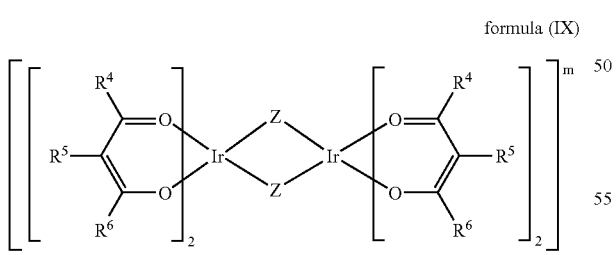

formula (IX)

where the symbols $R^1$, $R^2$, $R^4$, $R^5$, $R^6$ and Z are each as defined in claim 1 and in which
m is 2+, 1+, 0, 1− or 2−
and $Z^0$ is the same or different at each instance and is bipyridine, phenanthroline, ethylenediamine, propylenediamine, or 2-, 3- or 4-aminopyridine.

11. The process as claimed in claim 1, characterized in that the iridium(III)-containing reactant is a compound of the formula (VI), (VII), (VIII) and/or (IX) and

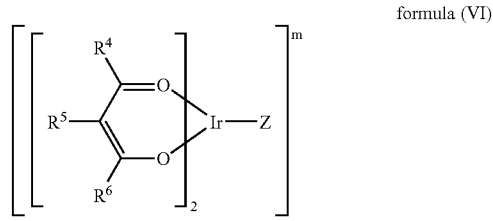

formula (VI)

where $R^4$, $R^5$ and $R^6$ are each as defined in claim 1 and where
Z is the same or different at each instance and is
and uncharged bidentate and/or bridging ligand $Z^0$,
a monoanionic bidentate and/or bridging ligand $Z^1$
or a dianionic bidentate and/or bridging ligand $Z^2$, and
m is 1+ when $Z=Z^0$, is 0 when $Z=Z^1$ and is 1− when $Z=Z^2$,

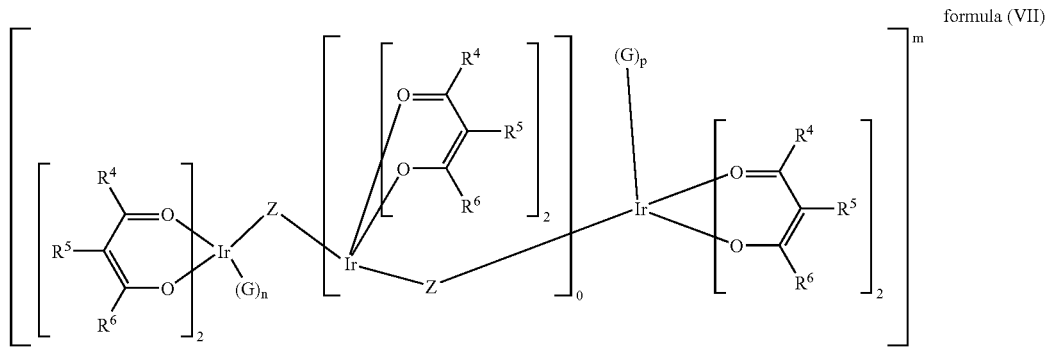

formula (VII)

where $R^4$, $R^5$ and $R^6$ are each as defined in claim 1,
G is the same or different at each instance and is either a monovalent anion X or an uncharged monodentate ligand Y,
n and p are the same or different at each instance and are 0 or 1,
o can assume integer values from 0 to 100 000 and
m may be from (o+2)+ to (o+2)−

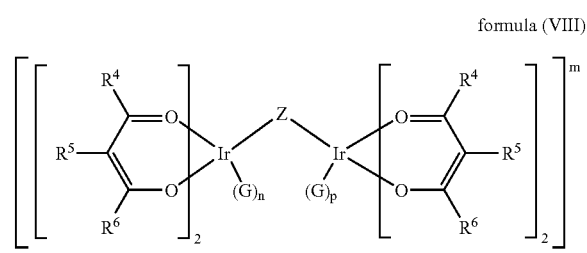

formula (VIII)

where the symbols and indices $R^4$, $R^5$ and $R^6$, G, Z, n and p are each as defined above, m is 2+, 1+, 0, 1– or 2– formula (IX)

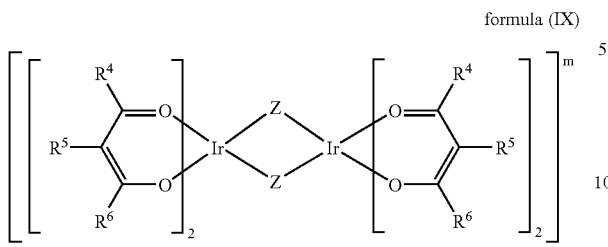

where the symbols $R^1$, $R^2$, $R^4$, $R^5$, $R^6$ and Z are each as defined in claim 1 and in which m is 2+, 1+, 0, 1– or 2–, $Z^1$ is the same or different at each instance and is diketonate, carboxylate, picolinate, aminocarboxylate, 1-ketoalkoxides, azide, cyanate, isocyanate, thiocyanate, isothiocyanate, chloride, bromide and iodide.

12. The process as claimed in claim 1, characterized in that the iridium(III)-containing reactant is a compound of the formula (VI), (VII), (VIII) and/or (IX) and formula (VI)

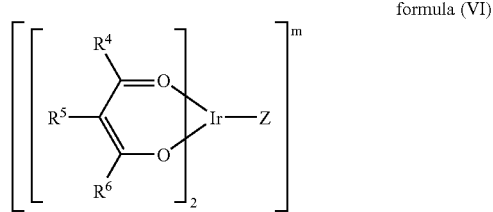

where $R^4$, $R^5$ and $R^6$ are each as defined in claim 1 and where

Z is the same or different at each instance and is
and uncharged bidentate and/or bridging ligand $Z^0$,
a monoanionic bidentate and/or bridging ligand $Z^1$
or a dianionic bidentate and/or bridging ligand $Z^2$, and
m is 1+ when Z=$Z^0$, is 0 when Z=$Z^1$ and is 1– when Z=$Z^2$, where $R^4$, $R^5$ and $R^6$ are each as defined in claim 1, G is the same or different at each instance and is either a monovalent anion X or an uncharged monodentate ligand Y, n and p are the same or different at each instance and are 0 or 1, o can assume integer values from 0 to 100 000 and m may be from (o+2)+ to (o+2)– formula (VIII)

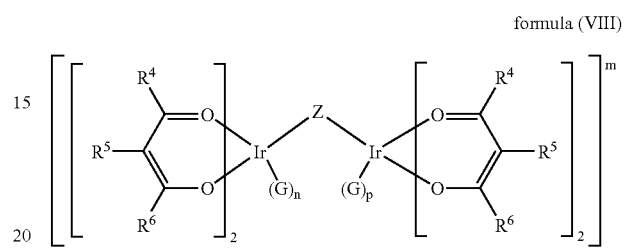

where the symbols and indices $R^4$, $R^5$ and $R^6$, G, Z, n and p are each as defined above, m is 2+, 1+, 0, 1– or 2– formula (IX)

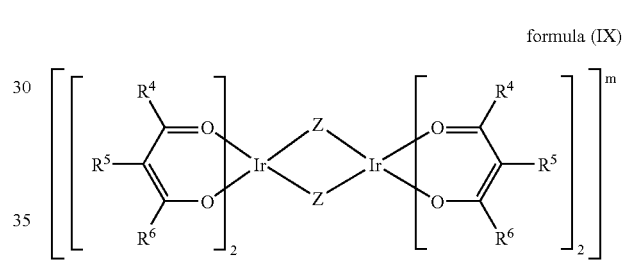

where the symbols $R^1$, $R^2$, $R^4$, $R^5$, $R^6$ and Z are each as defined in claim 1 and in which m is 2+, 1+, 0, 1– or 2–, formula (VII)

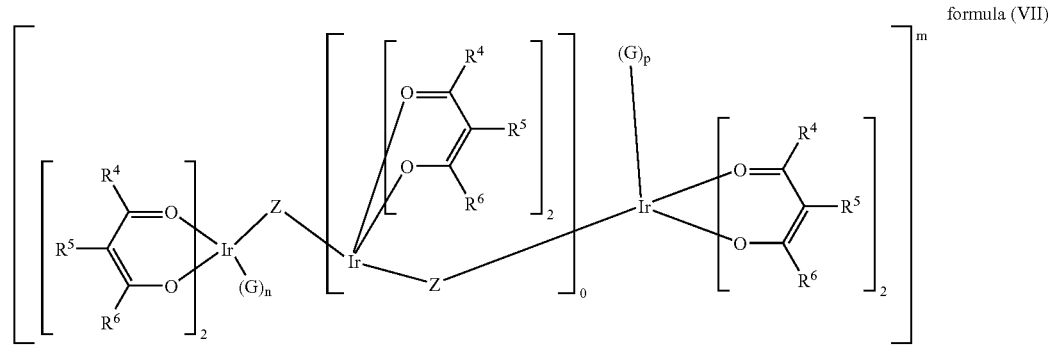

$Z^1$ is the same or different at each instance and is acetylacetonate or acetate.

13. The process as claimed in claim 1, characterized in that the iridium(III)-containing reactant is a compound of the formula (VI), (VII), (VIII) and/or (IX)

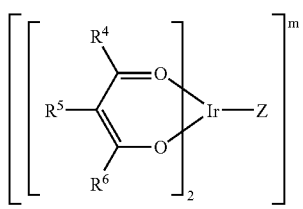

formula (VI)

where $R^4$, $R^5$ and $R^6$ are each as defined in claim 1 and where
Z is the same or different at each instance and is
and uncharged bidentate and/or bridging ligand $Z^0$,
a monoanionic bidentate and/or bridging ligand $Z^1$
or a dianionic bidentate and/or bridging ligand $Z^2$, and
m is 1+ when Z=$Z^0$, is 0 when Z=$Z^1$ and is 1− when Z=$Z^2$, m is 2+, 1+, 0, 1− or 2−

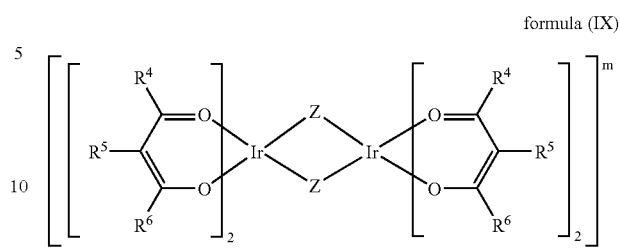

formula (IX)

where the symbols $R^1$, $R^2$, $R^4$, $R^5$, $R^6$ and Z are each as defined in claim 1 and in which
m is 2+, 1+, 0, 1− or 2−, and
$Z^2$ is the same or different at each instance and is oxalate, malonate, phthalate, isophthalate, terephthalate, oxide or peroxide.

14. The process as claimed in claim 7, characterized in that the iridium(III)-containing reactant is a compound of the formula (X) in which Q is Cl, Br, I or a diketonate.

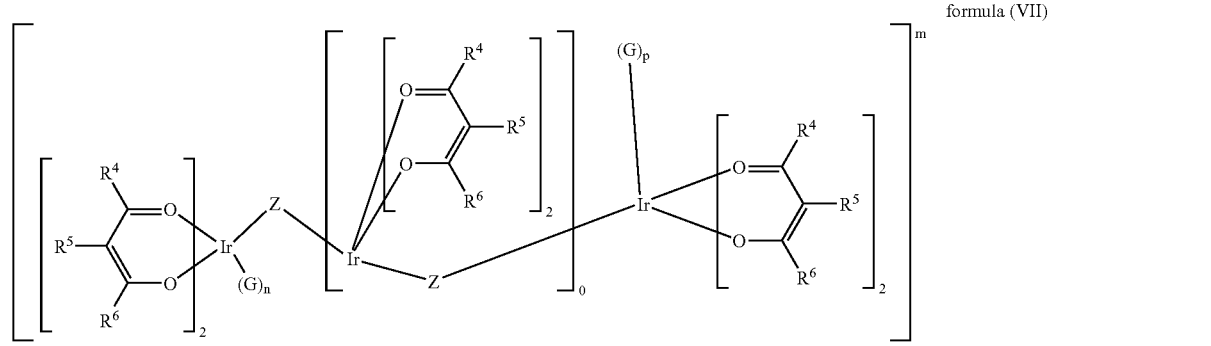

formula (VII)

where $R^4$, $R^5$ and $R^6$ are each as defined in claim 1,
G is the same or different at each instance and is either a monovalent anion X or an uncharged monodentate ligand Y,
n and p are the same or different at each instance and are 0 or 1,
o can assume integer values from 0 to 100 000 and
m may be from (o+2)+ to (o+2)−

15. The process as claimed in claim 1 claim 2, characterized in that the iridium(III)-containing reactant is a compound of the formula (V) in which X is the same or different at each instance and is a Cl, Br or I anion.

16. The process as claimed in claim 1, characterized in that the iridium(III)-containing reactant contains a compound of the formula (XI)

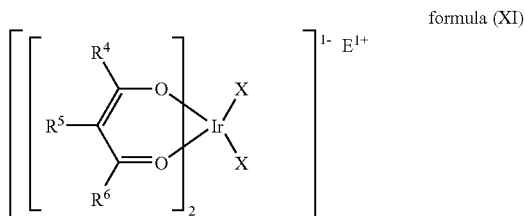

formula (XI)

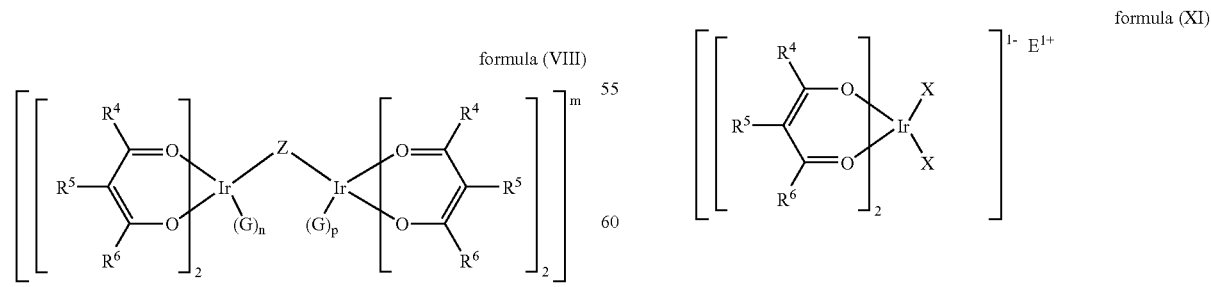

formula (VIII)

where the symbols and indices $R^4$, $R^5$ and $R^6$, G, Z, n and p are each as defined above, where $R^1$, $R^2$, $R^4$, $R^5$ and $R^6$ are each as defined in claim 1, X is the same or different at each instance and is a Cl, Br or I anion, and E is an alkali metal cation, ammonium or phosphonium ion.

17. The process as claimed in claim 1, characterized in that the iridium(III)-containing reactant used contains a mixture of at least 2 iridium(III)-containing reactants of the formula (II), or (V) to (XI)

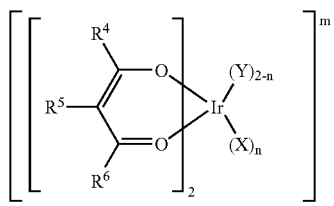

formula (V)

wherein

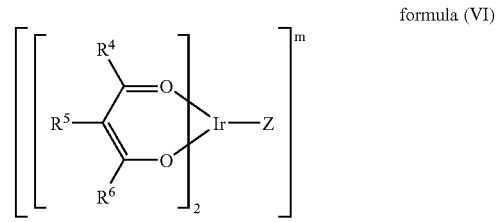

formula (VI)

where $R^4$, $R^5$ and $R^6$ are each as defined in claim 1 and where
 Z is the same or different at each instance and is
  and uncharged bidentate and/or bridging ligand $Z^0$,
  a monoanionic bidentate and/or bridging, ligand $Z^1$
  or a dianionic bidentate and/or bridging ligand $Z^2$, and
 m is 1+ when $Z=Z^0$, is 0 when $Z=Z^1$ and is 1– when $Z=Z^2$,

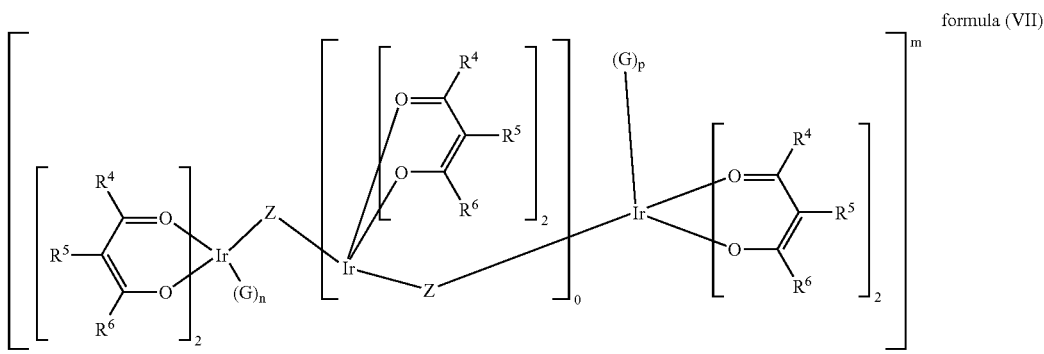

formula (VII)

$R^4$ and $R^6$ are the same or different at each instance and are a linear, branched or cyclic alkyl group having 1-20 carbon atoms, in which one or more nonadjacent $CH_2$ groups may be replaced by —O—, —S—, —$NR^1$—, —$CONR^2$—, —CO—O—, —$CR^1$=$CR^1$— or —C≡C—, and in which one or more hydrogen atoms may be replaced by F or aromatic groups each having from 3 to 14 carbon atoms, or an aryl and/or heteroaryl group having 3-20 carbon atoms or an alkoxy group $OR^1$, $R^5$ is the same or different at each instance and is a linear, branched or cyclic alkyl group having 1-20 carbon atoms, in which one or more nonadjacent $CH_2$ groups may be replaced by —O—, —S—, —$NR^1$—, —$CONR^2$—, —CO—O—, —$CR^1$=$CR^1$— or —C≡C—, and in which one or more hydrogen atoms may be replaced by F or aromatic groups each having from 3 to 14 carbon atoms, or an aryl and/or heteroaryl group having 3-20 carbon atoms, Y is the same or different at each instance and is an uncharged monodentate ligand, n is 0, 1 or 2 and m is 1– when n=2, is 0 when n=1 or is 1+ when n=0 where $R^4$, $R^5$ and $R^6$ are each as defined in claim 1,
 G is the same or different at each instance and is either a monovalent anion X or an uncharged monodentate ligand Y,
 n and p are the same or different at each instance and are 0 or 1,
 o can assume integer values from 0 to 100 000 and
 m may be from (o+2)+ to (o+2)–

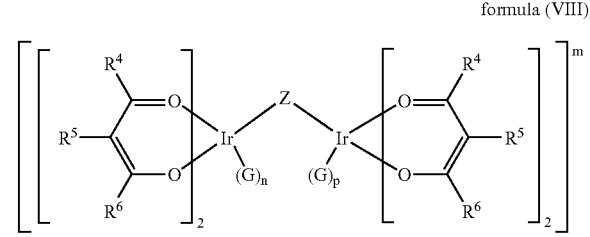

formula (VIII)

where the symbols and indices $R^4$, $R^5$ and $R^6$, G, Z, n and p are each as defined above, m is 2+, 1+, 0, 1– or 2–

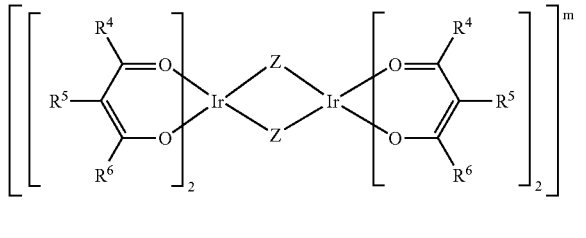

formula (IX)

where the symbols $R^1$, $R^2$, $R^4$, $R^5$, $R^6$ and Z are each as defined in claim 1 and in which m is 2+, 1+, 0, 1– or 2–, and

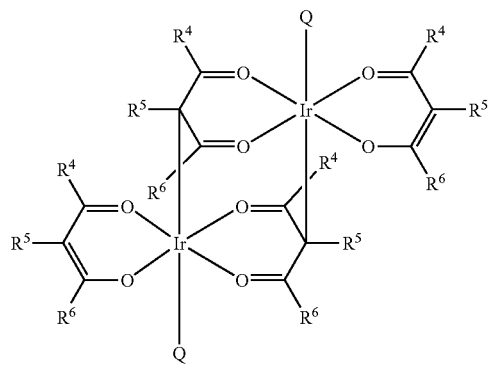

formula (X)

where the symbols $R^4$, $R^5$ and $R^6$ are each as defined in claim 1 and where Q is the same or different at each instance and is a monovalent anion

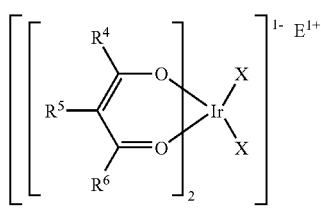

formula (XI)

where $R^1$, $R^2$, $R^4$, $R^5$ and $R^6$ are each as defined in claim 1, X is the same or different at each instance and is a Cl, Br or I anion, and E is an alkali metal cation, ammonium or phosphonium ion.

18. The process as claimed in claim 1, characterized in that the reactant used is a mixture which comprises at least one iridium(III)-containing reactant of the formula (II), or (V) to (XI)

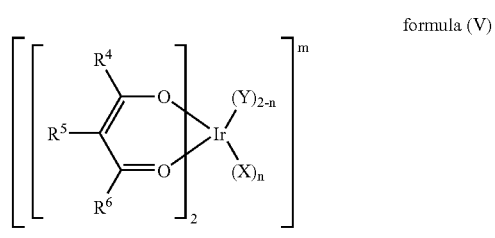

formula (V)

wherein $R^4$ and $R^6$ are the same or different at each instance and are a linear, branched or cyclic alkyl group having 1-20 carbon atoms, in which one or more nonadjacent $CH_2$ groups may be replaced by —O—, —S—, —$NR^1$—, —$CONR^2$—, —CO—O—, —$CR^1$=$CR^1$— or —C≡C—, and in which one or more hydrogen atoms may be replaced by F or aromatic groups each having from 3 to 14 carbon atoms, or an aryl and/or heteroaryl group having 3-20 carbon atoms or an alkoxy group $OR^1$, $R^5$ is the same or different at each instance and is a linear, branched or cyclic alkyl group having 1-20 carbon atoms, in which one or more nonadjacent $CH_2$ groups may be replaced by —O—, —S—, —$NR^1$—, —$CONR^2$—, —CO—O—, —$CR^1$=$CR^1$— or —C≡C—, and in which one or more hydrogen atoms may be replaced by F or aromatic groups each having from 3 to 14 carbon atoms, or an aryl and/or heteroaryl group having 3-20 carbon atoms, Y is the same or different at each instance and is an uncharged monodentate ligand, n is 0, 1 or 2 and m is 1– when n=2, is 0 when n=1 or is 1+ when n=0

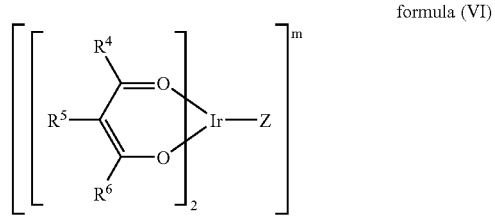

formula (VI)

where $R^4$, $R^5$ and $R^6$ are each as defined in claim 1 and where

Z is the same or different at each instance and is and uncharged bidentate and/or bridging ligand $Z^0$, a monoanionic bidentate and/or bridging ligand $Z^1$ or a dianionic bidentate and/or bridging ligand $Z^2$, and m is 1+ when Z=$Z^0$, is 0 when Z=$Z^1$ and is 1– when Z=$Z^2$,

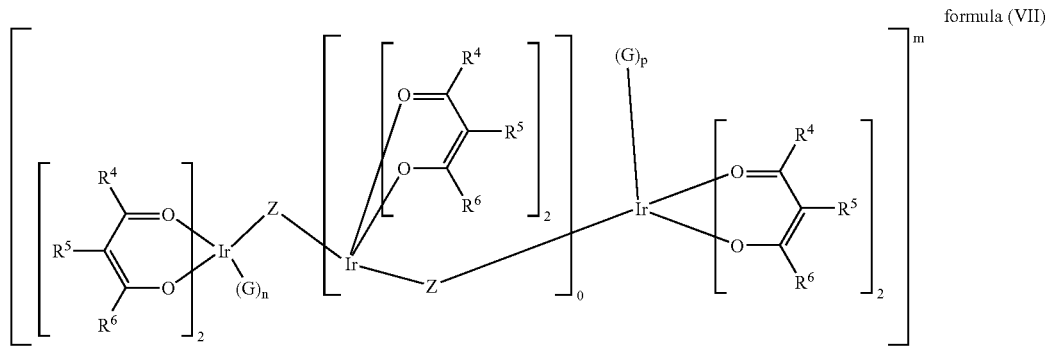

formula (VII)

where $R^4$, $R^5$ and $R^6$ are each as defined in claim 1,
- G is the same or different at each instance and is either a monovalent anion X or an uncharged monodentate ligand Y,
- n and p are the same or different at each instance and are 0 or 1,
- o can assume integer values from 0 to 100 000 and
- m may be from (o+2)+ to (o+2)−

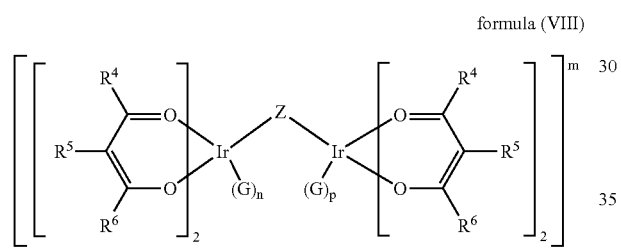

formula (VIII)

where the symbols and indices $R^4$, $R^5$ and $R^6$, G, Z, n and p are each as defined above,
  m is 2+, 1+, 0, 1− or 2−

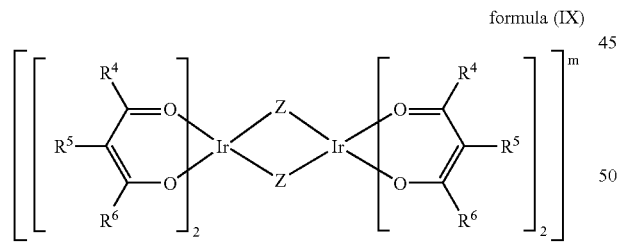

formula (IX)

where the symbols $R^1$, $R^2$, $R^4$, $R^5$, $R^6$ and Z are each as defined in claim 1 and in which m is 2+, 1+, 0, 1− or 2−, and

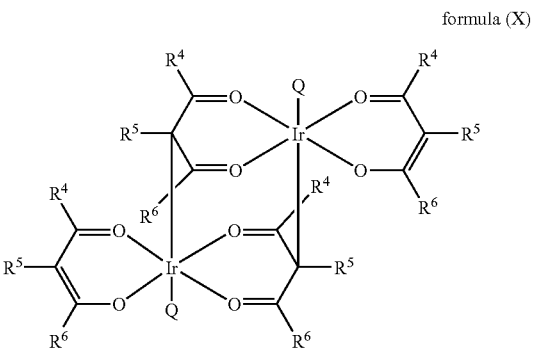

formula (X)

where the symbols $R^4$, $R^5$ and $R^6$ are each as defined in claim 1 and where
  Q is the same or different at each instance and is a monovalent anion

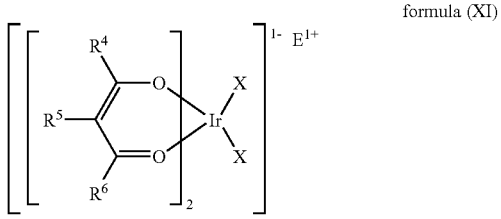

formula (XI)

where $R^1$, $R^2$, $R^4$, $R^5$ and $R^6$ are each as defined in claim 1. X is the same or different at each instance and is a Cl, Br or I anion, and E is an alkali metal cation, ammonium or phosphonium ion.

* * * * *